(12) United States Patent
Tsaur

(10) Patent No.: US 7,025,521 B2
(45) Date of Patent: Apr. 11, 2006

(54) APPLICATOR WITH TWO LIQUIDS

(76) Inventor: Garry Tsaur, 19222 Tranbarger St., Rowland Heights, CA (US) 91748

(*) Notice: Subject to any disclaimer, the term of this patent is extended or adjusted under 35 U.S.C. 154(b) by 396 days.

(21) Appl. No.: 10/661,995

(22) Filed: Sep. 12, 2003

(65) Prior Publication Data

US 2005/0058499 A1    Mar. 17, 2005

(51) Int. Cl.
*B43K 5/14*    (2006.01)
*B43K 5/00*    (2006.01)
*A61M 35/00*    (2006.01)

(52) U.S. Cl. .................. 401/132; 604/3; 401/205; 401/41

(58) Field of Classification Search ............... 401/132, 401/13, 205, 196, 40, 41, 47; 604/1, 2, 3
See application file for complete search history.

(56) References Cited

U.S. PATENT DOCUMENTS 5,490,736 A * 2/1996 Haber et al. ................. 401/40
5,927,884 A * 7/1999 Kao ........................... 401/132
6,729,786 B1 * 5/2004 Tufts et al. .................. 401/133

* cited by examiner

*Primary Examiner*—David J. Walczak
(74) *Attorney, Agent, or Firm*—Joe Nieh

(57) ABSTRACT

An applicator with two liquids comprising a hollow elongated tubular handle with a sealed end and an open end with an opening mechanism provided near the sealed end and an applicator tip affixed to one or both ends of the hollow elongated tubular handle. A first liquid is enclosed inside the hollow elongated tubular handle separated from the open end by a viscous substance and a second liquid is absorbed in the applicator tip. When air is allowed to enter near the sealed end through the opening mechanism, the first liquid in the hollow elongated tubular handle will flow through the viscous substance and commingle with the second liquid in the applicator tip to be applied.

14 Claims, 1 Drawing Sheet

APPLICATOR WITH TWO LIQUIDS

BACKGROUND—FIELD OF INVENTION

The present invention relates generally to a swab applicator. More specifically the present invention relates to a hollow tube swab applicator for storing and applying two liquids.

BACKGROUND—DESCRIPTION OF RELATED ART

Swab applicator generally comprises of a tubular handle with a formed absorbent tip at one or both ends of the tubular handle. The absorbent tip may be made of cotton or a foam absorbent material. The tubular handle may be made of wood, paper, or plastic and it may be solid or hollow.

Swab applicators have a variety of applications. Swab applicators are a convenient and sanitary means for applying a variety of substances such as liquids, lotions, creams, and various chemicals and medications. Generally the applicator tip of a dry swab applicator is first placed in contact with the liquid to be applied for the applicator tip to absorb the liquid. Subsequently, the moisturized applicator tip is placed in contact with the surface to apply the absorbed liquid to the surface. U.S. Pat. No. 5,702,035 issued to Tsao shows one design wherein the hollow tubular handle encloses a liquid that can be subsequently released into the applicator tip for application. However, the swab applicator with a hollow tubular handle disclosed in U.S. Pat. No. 5,702,035 only contains one liquid. Some applications require two separate liquids to be stored separately and mixed just prior to application or applied in sequence.

SUMMARY OF THE INVENTION

The present invention is an applicator with two liquids comprising a hollow elongated tubular handle with a sealed end and an open end with an applicator tip affixed to one or both ends of the hollow elongated tubular handle. An opening means is provided near the sealed end of the hollow elongated tubular handle. A first liquid is enclosed inside the hollow elongated tubular handle separated from the open end by a viscous substance and a second liquid is absorbed in the applicator tip. When air is allowed to enter near the sealed end through the opening means and where the applicator tip is only partially saturated with the second liquid, the first liquid in the hollow elongated tubular handle will flow through the viscous substance and commingle with the second liquid in the applicator tip to be applied. If the applicator tip is saturated with the second liquid, the first liquid will not immediately flow into the applicator tip but, instead, the second liquid will be first partially depleted through application before the first liquid will flow into the applicator tip for application.

DETAILED DESCRIPTION OF THE PREFERRED EMBODIMENT

Figure 1:
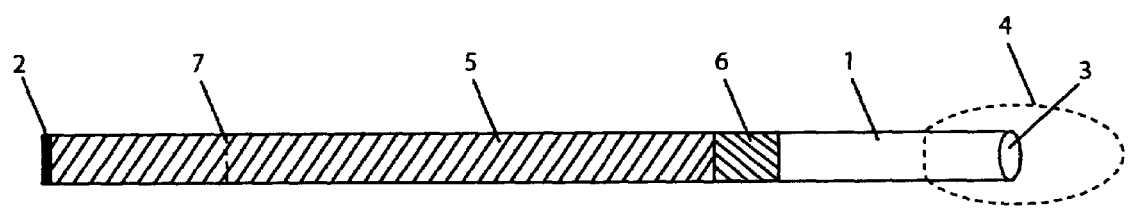
FIG. 1 shows the preferred embodiment of the applicator with two liquids.

FIG. 1 shows the preferred embodiment of the present invention. In the preferred embodiment, the applicator with two liquids comprises of a hollow elongated tubular handle 1 with a sealed end 2 and an open end 3. An applicator tip 4 is affixed to the open end 3 of the hollow elongated tubular handle 1. A first liquid 5 is disposed within the hollow elongated tubular handle 1 separated from the open end 3 by a viscous substance 6. The preferred viscous substance 6 is silicone but other suitable viscous substance may also be utilized. An opening means 7 such as a score line is positioned near the sealed end 2.

A second liquid is absorbed into the applicator tip 4. If the second liquid is non-evaporative, such as oil-based liquid, the applicator tip 4 will not require further packaging to prevent evaporation of the second liquid. If the second liquid is an evaporative liquid, such as water-based liquid or alcohol, additional packaging may be necessary to prevent evaporation of the second liquid from the applicator tip 4.

Furthermore, if the applicator tip 4 is fully saturated with the second liquid the applicator tip 4 may act as a stopper and prevent the exit of the first liquid 5 at the first instance of opening. In this instance, the second liquid will have to be applied first. Upon partial depletion of the second liquid, the first liquid 5 will then begin to flow into the applicator tip for application next. This embodiment is particularly suited for applications where one liquid, such as rust remover or cleaner, must be applied first before a second liquid, such as a lubricant or a protectant is to be applied. The applicator tip 4 may also be partially moistened with the second liquid to allow the first liquid 5 to flow and exit the hollow elongated tubular handle 1 and to commingle with the second liquid to be applied at the same time. This embodiment is particularly suitable for applications where two separate liquids must be mixed and used together.

Upon opening of the hollow elongated tubular handle 1 at the opening means 7 the first liquid 5 will flow through the viscous substance 6, which will spread open and adhere to the inside of the hollow elongated tubular handle 1 and remain essentially at its original position, and into the absorbent tip 4 to commingle with the second fluid for application.

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. An applicator with two liquids comprising a hollow elongated tubular handle with a sealed end and an open end with an opening means positioned near the sealed end and an applicator tip affixed to said open end of the hollow elongated tubular handle with a first liquid disposed within the hollow elongated tubular handle separated from the open end by a viscous substance and a second liquid absorbed into said applicator tip wherein upon opening of the hollow elongated tubular handle through the opening means, the first liquid will flow through the viscous substance and into the said absorbent tip for application with the second liquid.

2. An applicator with two liquids as in claim 1, wherein a second applicator tip is affixed to said sealed end of the hollow elongated tubular handle.

3. An applicator with two liquids as in claim 1, wherein the applicator tip is made of an absorbent material.

4. An applicator with two liquids as in claim 3, wherein said opening means is a score line.

5. An applicator with two liquids as in claim 3, wherein said viscous substance is silicone.

6. An applicator with two liquids as in claim 1, wherein said opening means is a score line.

7. An applicator with two liquids as in claim 6, wherein said viscous substance is silicone.

8. An applicator with two liquids as in claim 1, wherein said viscous substance is silicone.

9. An applicator with two liquids as in claim 1, wherein said applicator tip is saturated with said second liquid.

10. An applicator with two liquids as in claim 1, wherein said applicator tip is only partially saturated with said second liquid.

11. An applicator with two liquids comprising a hollow elongated tubular handle with a sealed end and an open end with a frangible section positioned near the sealed end and an absorbent applicator tip affixed to said open end of the hollow elongated tubular handle with a first liquid disposed within the hollow elongated tubular handle separated from the open end by silicone and a second liquid absorbed into said applicator tip wherein upon opening of the hollow elongated tubular handle through the frangible section, the first liquid will flow through the silicone and into the said absorbent tip for application with the second liquid.

12. An applicator with two liquids as in claim 11, wherein a second applicator tip is affixed to said sealed end of the hollow elongated tubular handle.

13. An applicator with two liquids as in claim 11, wherein said applicator tip is saturated with said second liquid.

14. An applicator with two liquids as in claim 11, wherein said applicator tip is only partially saturated with said second liquid.

* * * * *